(12) United States Patent
Wilson et al.

(10) Patent No.: US 9,075,900 B2
(45) Date of Patent: Jul. 7, 2015

(54) SYSTEMS, METHODS AND COMPUTER PROGRAM PRODUCTS FOR PROVIDING COMPLIANT DELIVERY OF CONTENT, APPLICATIONS AND/OR SOLUTIONS

(75) Inventors: Benjamin Michael Wilson, Victoria (CA); Michael Hansen, Apex, NC (US)

(73) Assignee: Exco InTouch, Nottingham (GB)

( * ) Notice: Subject to any disclaimer, the term of this patent is extended or adjusted under 35 U.S.C. 154(b) by 193 days.

(21) Appl. No.: 13/459,573

(22) Filed: Apr. 30, 2012

(65) Prior Publication Data

US 2012/0295550 A1 Nov. 22, 2012

Related U.S. Application Data

(60) Provisional application No. 61/487,426, filed on May 18, 2011.

(51) Int. Cl.
*G06F 19/00* (2011.01)
*G06Q 50/24* (2012.01)
*H04W 12/02* (2009.01)

(52) U.S. Cl.
CPC .............. *G06F 19/322* (2013.01); *G06Q 50/24* (2013.01); *H04W 12/02* (2013.01)

(58) Field of Classification Search
CPC ..... G06Q 10/10; G06Q 50/20; G06Q 20/325; G06Q 20/108; G06F 19/345; H04W 8/26; H04W 92/18; H04W 4/206; H04W 52/0254; H04W 76/02; H04W 88/06; H04W 36/30; H04W 84/12; H04W 88/04; H04W 8/12; H04W 8/183; H04W 8/245; H04M 1/7253; H04M 11/066; H04M 1/72544

USPC .......................................... 715/150; 705/2, 3
See application file for complete search history.

(56) References Cited

U.S. PATENT DOCUMENTS

| | | | |
|---|---|---|---|
| 6,095,985 A * | 8/2000 | Raymond et al. ............. | 600/513 |
| 2003/0085038 A1* | 5/2003 | Restarick et al. ............. | 166/278 |
| 2005/0038680 A1* | 2/2005 | McMahon ........................ | 705/3 |
| 2006/0004609 A1* | 1/2006 | Kenneth et al. .................... | 705/3 |
| 2006/0167346 A1* | 7/2006 | Sarel ............................. | 600/300 |
| 2007/0106565 A1* | 5/2007 | Coelho ........................... | 705/26 |
| 2008/0004904 A1* | 1/2008 | Tran ................................. | 705/2 |
| 2008/0021741 A1* | 1/2008 | Holla et al. ........................ | 705/3 |
| 2008/0097908 A1* | 4/2008 | Dicks et al. ..................... | 705/50 |
| 2008/0097910 A1* | 4/2008 | Dicks et al. ..................... | 705/50 |
| 2008/0119705 A1* | 5/2008 | Patel et al. .................... | 600/347 |
| 2008/0194925 A1* | 8/2008 | Alsafadi et al. ............... | 600/301 |
| 2008/0221466 A1* | 9/2008 | Brauers et al. ................. | 600/508 |
| 2008/0263048 A1* | 10/2008 | Wise ................................ | 707/9 |
| 2009/0318779 A1* | 12/2009 | Tran ............................... | 600/301 |
| 2010/0010358 A1* | 1/2010 | Boute et al. .................... | 600/509 |
| 2010/0145730 A1* | 6/2010 | Abreu ............................... | 705/3 |
| 2010/0279718 A1* | 11/2010 | Borve ........................... | 455/466 |
| 2011/0108623 A1* | 5/2011 | Hammad ....................... | 235/382 |

(Continued)

*Primary Examiner* — Nizar Sivji
(74) *Attorney, Agent, or Firm* — Myers Bigel Sibley & Sajovec, P.A.

(57) ABSTRACT

Systems, methods and computer program products for providing device independent compliant applications include accumulating device, user and/or peripheral interface data corresponding to a mobile terminal of a user and associating the device, user and/or peripheral interface data with a unique identifier and storing the device, user and/or peripheral interface data and the unique identifier in a database. Before storing the device, user and/or peripheral interface data, the device, user and/or peripheral interface data is de-identified from the user.

29 Claims, 7 Drawing Sheets

(56) References Cited

U.S. PATENT DOCUMENTS

| | | | |
|---|---|---|---|
| 2011/0119155 A1* | 5/2011 | Hammad et al. | 705/26.41 |
| 2011/0152656 A1* | 6/2011 | Weinert et al. | 600/365 |
| 2011/0161111 A1* | 6/2011 | Dicks et al. | 705/3 |
| 2011/0172550 A1* | 7/2011 | Martin et al. | 600/523 |
| 2011/0191245 A1* | 8/2011 | Ricciardi et al. | 705/51 |
| 2011/0202368 A1* | 8/2011 | Stakutis et al. | 705/3 |
| 2011/0208529 A1* | 8/2011 | Jeal et al. | 705/1.1 |
| 2011/0213225 A1* | 9/2011 | Bernstein et al. | 600/309 |
| 2011/0251469 A1* | 10/2011 | Varadan | 600/301 |
| 2012/0010518 A1* | 1/2012 | Sarel | 600/529 |
| 2012/0018506 A1* | 1/2012 | Hammad et al. | 235/375 |
| 2012/0041767 A1* | 2/2012 | Hoffman et al. | 705/1.1 |
| 2012/0041786 A1* | 2/2012 | Yu | 705/3 |
| 2012/0084210 A1* | 4/2012 | Farahmand | 705/64 |
| 2012/0205441 A1* | 8/2012 | Utech et al. | 235/376 |
| 2012/0232929 A1* | 9/2012 | Experton | 705/3 |
| 2012/0253847 A1* | 10/2012 | Dell'Anno et al. | 705/3 |
| 2013/0159021 A1* | 6/2013 | Felsher | 705/3 |

* cited by examiner

US 9,075,900 B2

SYSTEMS, METHODS AND COMPUTER PROGRAM PRODUCTS FOR PROVIDING COMPLIANT DELIVERY OF CONTENT, APPLICATIONS AND/OR SOLUTIONS

RELATED APPLICATIONS

This non-provisional patent application claims priority to U.S. provisional patent application 61/487,426, filed May 18, 2011, entitled "SYSTEMS, METHODS AND COMPUTER PROGRAM PRODUCTS FOR PROVIDING COMPLIANT DELIVERY OF CONTENT, APPLICATIONS AND/OR SOLUTIONS", the disclosure of which is incorporated herein in its entirety by reference.

FIELD OF THE INVENTION

The present invention relates generally to communication and, more particularly, to systems, methods and computer program products for delivery of applications.

BACKGROUND

Many industries may utilize and/or rely on communications with multiple classes of users. For example, the healthcare and pharmaceutical industries may rely on communications between various classes including healthcare providers, such as doctors and/or nurses, patients, prospective patients, and/or clients, such as, for example, healthcare research organizations, medical device manufacturers and/or pharmaceutical companies, among others. Advances in technology have provided for wireless communication systems using, for example, mobile terminals. However, functionality of mobile terminals may vary as a function of hardware, software, and/or services, among others. Accordingly, currently available systems and methods may not be suitable for providing ubiquitous mobile applications through the various mobile terminals.

SUMMARY

Some embodiments of the present invention are directed to methods of providing device independent compliant applications. Such methods may include receiving device data corresponding to a mobile device that is operable to be connected to a solution provider, receiving user data corresponding to the user of the mobile device, and receiving peripheral interface data that corresponds to peripheral devices that may interface with the mobile device corresponding to a user function. Methods may include associating the device data, the user data and the peripheral interface data with a unique identifier, encrypting at least a portion of the device data, the user data, and/or the peripheral interface data, and storing the unique identifier and at least a portion of the device data, the user data and/or the peripheral data. In some embodiments, at least one of receiving device data, receiving, user data, receiving peripheral interface data, associating the device data, the user data and the peripheral interface data, the encrypting and the storing is performed using at least one processor.

In some embodiments, receiving the device data includes receiving device manufacturer identification data, a device model number, a device version identifier, and/or at least one display capability. Some embodiments provide that receiving the device data includes receiving types and/or formats of supported media, at least one media streaming capability, image capturing functionality, a multimedia messaging service (MMS) capability and/or a digital rights management capability. Some embodiments provide that receiving the device data includes receiving data corresponding to installed and/or supported applications and/or browser related data including user agent and user agent profile. In some embodiments, receiving the device data includes receiving a communication capability including at least one of a near field communication (NFC) capability, a wireless and/or wired network communication capability, and a communication network capability. Some embodiments provide that receiving the device data includes receiving at least one of data corresponding to markup languages, location awareness capability, encryption functionality, and security features.

In some embodiments, receiving the user data corresponding to the user of the mobile device includes receiving personal identification data including name, gender, ethnicity, date of birth, place of birth, citizenship, subscriber identity module (SIM) card identifier, residence information, mobile terminal numerical identifier, a country or region, and/or a language preference. In some embodiments, receiving the user data corresponding to the user of the mobile device includes receiving a list of installed and/or accessed applications, an identifier corresponding to a third party application, and/or communication service terms.

Some embodiments provide that receiving the peripheral interface data includes receiving parental interface identifiers, device sensor interfaces, and/or device alerts. In some embodiments, receiving the peripheral interface data includes receiving data corresponding to medical diagnostic devices. Some embodiments provide that receiving the peripheral interface data includes receiving a batch of peripheral interface data that is logged and stored by at least one of the peripheral devices. Some embodiments provide that receiving the peripheral device data includes receiving a first subset of the peripheral interface data that is compliant in a first regulatory environment, wherein a second subset of the peripheral interface data that is different from the first subset of peripheral interface data is excluded.

Some embodiments further include receiving updated device data, updated user data and/or updated peripheral interface data and storing the unique identifier and at least a portion of the updated device data, the updated user data and/or the updated peripheral interface data.

Yet further embodiments include generating an audit trail that is associated with operations corresponding to device data, user data, peripheral interface data, and/or the unique identifier.

Some embodiments of the present invention include methods of providing device independent compliant applications, such methods include accumulating device, user and/or peripheral interface data corresponding to a mobile terminal of a user, associating the device, user and/or peripheral interface data with a unique identifier and storing the device, user and/or peripheral interface data and the unique identifier in a database, and before storing the device, user and/or peripheral interface data, de-identifying the device, user and/or peripheral interface data.

In some embodiments, accumulating device, user and/or peripheral interface data includes receiving device manufacturer identification data, a device model number, a device version identifier, and/or at least one display capability. Some embodiments provide that accumulating device, user and/or peripheral interface data includes receiving types and/or formats of supported media, at least one media streaming capability, image capturing functionality, a multimedia messaging service (MMS) capability, data corresponding to installed and/or supported applications and/or browser related data including user agent and user agent profile, a communication capability including at least one of a near field communication (NFC) capability, a wireless and/or wired network communication capability, and/or a communication network capability.

In some embodiments, accumulating device, user and/or peripheral interface data includes receiving personal identification data, a list of installed and/or accessed applications, an identifier corresponding to a third party application, and/or communication service terms. Some embodiments provide that accumulating device, user and/or peripheral interface data includes receiving parental interface identifiers, device sensor interfaces, device alerts, data corresponding to medical diagnostic devices and/or a batch of peripheral interface data that is logged and stored by at least one of the peripheral devices.

Some methods according to the present invention include generating an audit trail that is associated with operations corresponding to device data, user data, peripheral interface data, and/or the unique identifier.

In some embodiments, de-identifying the device, user and/or peripheral interface data includes encrypting at least a portion of the device, user and/or peripheral interface data and storing the encrypted data in association with the unique identifier. Some embodiments provide that de-identifying the device, user and/or peripheral interface data includes encrypting at least one of a plurality of data field identifiers under which the encrypted data is stored.

Some embodiments further include determining a type and/or format responsive to the device, user and/or peripheral interface data.

Some embodiments of the present invention are directed to methods of providing device independent compliant applications. Such methods may include detecting a user via a mobile terminal, checking for known performance issues corresponding to the mobile terminal, determining, responsive to determining a performance issue, a type of performance issue and sending at least one message corresponding to the type of performance issue.

Some embodiments provide that the type of performance issue is determined to be a technical issue and that sending the at least one message includes sending at least one message including a technical instruction and/or data file to the user.

In some embodiments, the type of performance issue is determined to be an incompatibility issue and that sending the at least one message includes sending at least one message including incompatibility instructions to the user and/or to a third party. Some embodiments provide that the incompatibility instructions include a message for the user to provide to a third party.

Some embodiments provide that the type of performance issue is determined to be a training issue and that sending the at least one message includes sending at least one message including training instructions to the user and/or to a third party.

In some embodiments, the type of performance issue includes at least one of a technical issue, a compatibility issue and/or a training issue.

Some embodiments of the present invention are directed to computer program products that include a computer-readable medium having executable computer-readable program code therein, the computer-readable program code being configured to implement operations according to the methods disclosed herein.

Some embodiments are directed to systems that include modules that are configured to perform operations as disclosed herein.

It is noted that aspects of the invention described with respect to one embodiment, may be incorporated in a different embodiment although not specifically described relative thereto. That is, all embodiments and/or features of any embodiment can be combined in any way and/or combination. These and other objects and/or aspects of the present invention are explained in detail in the specification set forth below.

BRIEF DESCRIPTION OF THE DRAWINGS

The accompanying figures are included to provide a further understanding of the present invention, and are incorporated in and constitute a part of this specification. The drawings illustrate some embodiments of the present invention and, together with the description, serve to explain principles of the present invention.

DETAILED DESCRIPTION

Figure 1:
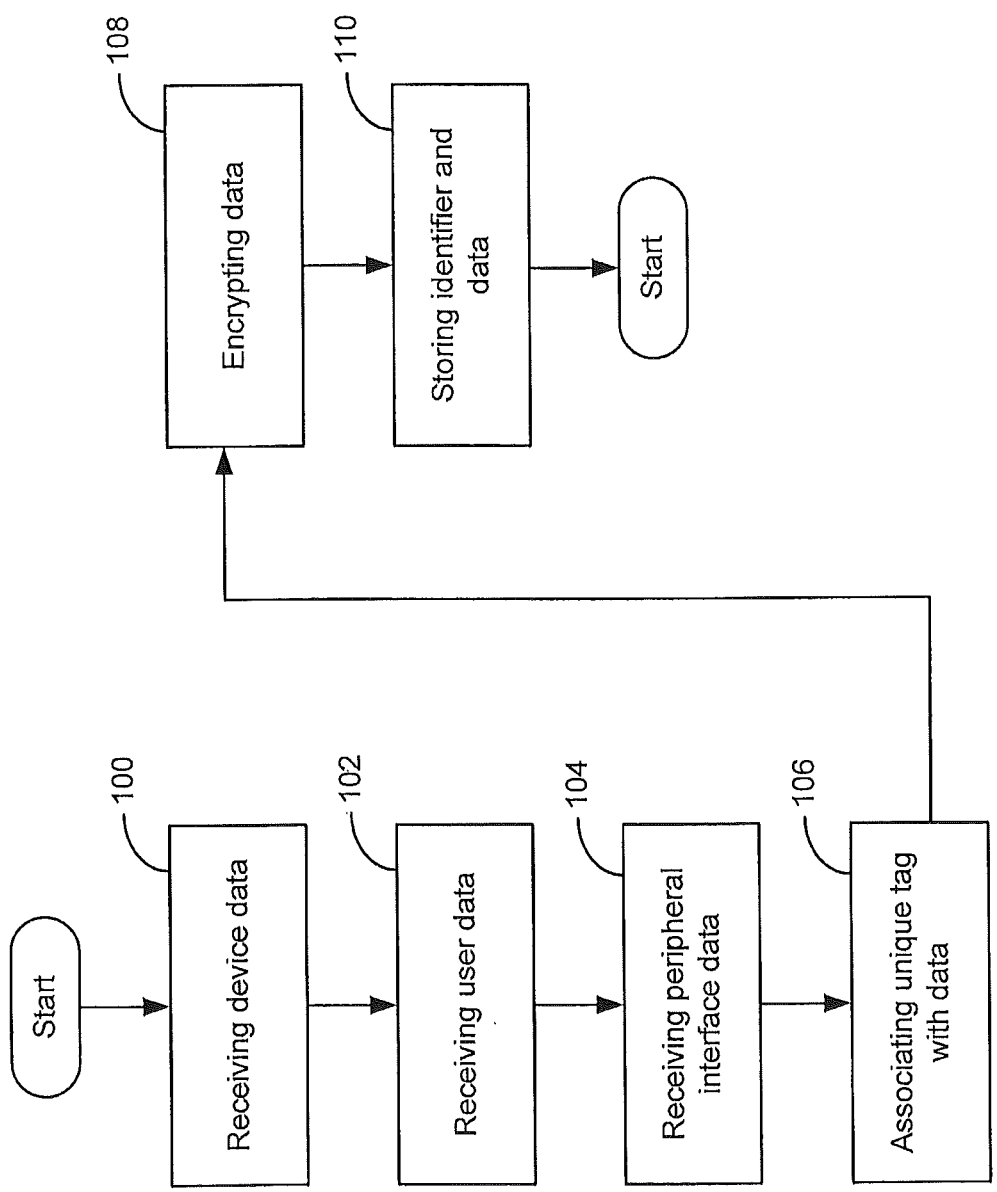
FIG. 1 is a block diagram illustrating operations for providing device independent compliant applications according to some embodiments of the present invention.

The present invention now is described more fully hereinafter with reference to the accompanying drawings, in which some embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. As used herein, the term "and/or" includes any and all combinations of one or more of the associated listed items.

Pursuant to embodiments of the present invention, systems and methods are provided for providing compliant messaging services. Compliance may be required for applications used in, for example, healthcare and/or pharmaceutical industries. In some embodiments, a sponsor, such as a pharmaceutical provider, for example, may initiate and/or manage a campaign such as, for example, a clinical and/or marketing study regarding a new drug and/or drug application and/or disease condition. In some embodiments, a campaign may include a prescription reminder service, health surveys and/or questionnaires, and/or services for increasing the patient's compliance with a clinical study or drug regimen. In this regard, a campaign may include a series of events and/or operations undertaken to achieve a specific goal. As described herein, campaigns may be directed to gathering and/or disseminating information and/or data corresponding to a clinical and/or marketing study regarding a new drug and/or drug application, disease condition and/or a prescription reminder service, among others. Concomitant with such studies may be strict requirements including audit trails, validation, authentication and/or confidentiality, among others. Additionally, as a practical matter, global connectivity, sufficient encryption and performance, multi-lingual capability and/or integration flexibility may be necessary as well. In this regard, a trusted third party to manage the management, data, communications, and/or compliance issues associated with such campaigns may be beneficial. For example, in some regulatory environments, sponsors may be prohibited from having direct contact with and/or storing any customer, subject and/or patient data, among others. Some embodiments as described herein may be used in conjunction with and/or may benefit from information disclosed in pending patent application Ser. No. 12/434,244 filed May 1, 2009, entitled "Systems, Methods and Computer Program Products For Providing Compliant Messaging Services", the contents of which are incorporated by reference as if entirely set forth herein.

In some embodiments of the present invention, the solutions and/or applications may be delivered to users via mobile terminals. By way of example, some solutions and/or applications may be healthcare solutions and/or healthcare applications and thus may be subject to compliance with regulations, laws and/or rules corresponding to one or more governmental agencies and/or jurisdictions. However, the mobile terminals may vary in capability and/or configuration. As such, methods systems and computer program products described herein provide device independent compliant delivery of solutions and/or applications.

Embodiments disclosed herein may provide systems, methods and computer program products for providing personal care for a patient and/or user. For example, as described herein, patient treatment may be personalized by compliantly using personalized technology. In this manner, embodiments disclosed herein may dynamically launch mobile content, solutions and/or applications that are catered to user and/or patient specific needs, which may be identified in terms of individual and/or technological capabilities.

Reference is now made to FIG. 1, which is a block diagram illustrating operations for of providing device independent compliant applications according to some embodiments of the present invention. Operations include receiving device data corresponding to a mobile device that is operable to be connected to a solution provider (block 100). As described herein, the device, user and peripheral interface data collectively may be referred to using a biological term that describes the long-term storage of information, namely "DNA". As applied to the collection of data corresponding to mobile terminals and/or users, the information may collectively be referred to as mDNA herein. In this regard, the capabilities of mobile devices may be referred to as mobile device "chromosomes". As used herein, a solution provider may include a provider of operations corresponding to mDNA and/or services related thereto. In some embodiments, mDNA may be used as a look-up reference for properties, data and/or information that may be used to determine and/or identify regulatory compliance issues. Some embodiments provide that mDNA and/or operations associated therewith may be used by a solution provider and/or third parties that may be provided access thereto to provide related services.

In that regard, device data may also be referred to as device chromosomes and may include, for example, device manufacturer identification, device model number and/or version identifier, display capability including display size, resolution, and/or color capability, among others. In some embodiments device chromosomes may include types and/or formats of supported media, media streaming capabilities, camera, video and/or other image capturing functionality, multimedia messaging service (MMS) capabilities and digital rights management capabilities. Some embodiments provide that device chromosomes may include data corresponding to installed and/or supported applications including, but not limited to Framework versions such as Android version, iOS version, BlackBerry OS version, Windows Phone OS version, Java MIDP version, and/or types of applications supported. Device chromosomes may further include browser related data including user agent and user agent profile, whether the browser is markup, client-side script (eg JavaScript, WML Script) and/or style sheet enabled, including markup version/type, client-side script version/type, style sheet version/type, and/or plug-ins such as Silverlight, Flash and their versions and/or toolkits such as Edge, JQuery, etc. The browser engine type, such as AppleWebKit or Trident and their versions may be captured according to some embodiments.

Device chromosomes may include communication capabilities including near field communication (NFC) capabilities, such as RFID, BlueTooth, and/or Zigbee, among others, wireless and/or wired network communication capabilities including 10/100 Ethernet and/or WiFi connectivity, communication network capabilities including GSM, GPRS, EDGE, 3G, 4G, WiMax, LTE, 5G, and/or satellite, among others. Additionally, device chromosomes may include network name, network signal strength and/or signal quality data.

Device chromosomes may further include data corresponding to markup languages such as HTML, XHTML, WML, and HTML5 support and firmware version data and location awareness support, such as, GPS, IP geo-location, cell tower proximity, signal triangulation and/or other location determination technologies. Additionally, some embodiments provide that device chromosomes include transmission encryption functionality, data encryption functionality, and/or security features that are installed on the device and/or that are associated with applications that are installed thereon. Further, device chromosomes may include data corresponding to one or more user profiles than may be installed on the mobile terminal. As such, the profile information may be used in combination with other personal security keys to ensure the correct identity of the user. In this manner, other users of the same mobile terminal may not access or be accessed in the context of the compliant solution and/or application provision.

In addition to receiving device chromosomes, user data, also referred to herein as user chromosomes, may be received (block 102). User chromosomes may include communication related chromosomes and personal identification chromosomes. Examples of personal identification chromosomes may include names, gender, ethnicity, date of birth, place of birth, citizenship, subscriber identity module (SIM) card identifier, and/or residence information including street address, city, state and/or postal/zip code. Some embodiments of communication related chromosomes include a mobile terminal numerical or email address and/or phone number, the country or region (e.g., Canada, which has French and English languages) in which the mobile terminal is located and/or in which communication services originate, a language preference and/or media access control (MAC) addresses and/or ethernet hardware addresses (EHA) corresponding to wireless short range and/or NFC communications. Some embodiments provide that user chromosomes may include lists of installed and/or accessed applications and versions thereof. Additionally, user chromosomes may include identifiers corresponding to third party applications including, for example, Twitter, Skype, BlackBerry, and/or Facebook among others. User chromosomes may further include communication service terms including contract type (monthly, annual, prepaid, etc.), and a defined service area and/or areas identified based on signal strength and/or quality.

Operations may include receiving peripheral interface data, which may be referred to as peripheral interface chromosomes (block 104). Peripheral chromosomes may include parental interface identifiers, device sensor interfaces, device alerts, etc. Examples of peripheral devices include body area networks (BANs) wireless body area networks, spirometers, thermometers, blood pressure cuffs, and/or other wired and/or wireless devices including medical diagnostic devices, hubs etc. For example, a hub may include a device that may transmit and/or receive data to and/or from multiple devices. In this manner, connections from a device such as a mobile terminal to multiple devices may be managed. For example, a hub may be helpful in managing connections between a mobile terminal and one or more peripheral devices.

Peripheral device chromosomes may include identification information and/or functional information corresponding to the peripheral devices. Some embodiments provide that the peripheral interface chromosomes corresponding to the peripheral devices may be stored in a separate and/or integrated peripheral device database. As such, the peripheral chromosomes may be associated with and/or stored with a user's and/or user device's mDNA. Peripheral interface chromosomes may include interface information such as connectivity data for wired and or wireless devices including those connected via local area network (LAN), wireless local area network (WLAN), wide area network (WAN), personal area network (PAN), body area network (BAN) and/or near field communication (NFC) devices such as BlueTooth, among others. In some embodiments, each peripheral device may be provided and/or represented by a dedicated and/or shared data stream and/or signal. Additionally, some embodiments provide that data may be captured and logged, to be uploaded in a batch. Additionally, preventative alerts may be generated responsive to one or more measurements or data acquired via the peripheral devices and/or interfaces. Some embodiments provide that the user may be able to determine their own level of consent (i.e., how much data they wish to provide to the service.) In this manner, a user may decide what data to provide that may be useful and/or necessary in effectively managing their condition.

In some embodiments, collection, gathering, and/or detection of some and/or all of the data corresponding to chromosomes in the mDNA may be conditioned on full and/or partial consent. For example, some jurisdictions and or regulatory environments proscribe that users must opt-in and/or be permitted to opt-out of the collection, gathering, and/or detection of the mDNA chromosomes. As such, some embodiments provide that consent policies corresponding to specific users may be determined using a geography-specific identifier.

In some embodiments, consent policies may provide multiple levels of consent with varying degrees of granularity. For example, some embodiments may include three levels of consent that correspond to different types and/or classes of data. In such embodiments, a first level of consent may correspond to device specific information regarding a specific device and/or type. Some embodiments provide that device specific information or portions thereof may also be publically available information. A second level of consent may correspond to device personalization information. For example, device personalization information may include information regarding the applications and/or configurations of a device that are specific to the device of a specific user. Continuing with the present example, a third level of consent may correspond to personal information of the user. The personal information may include personal information that is stored and/or transmitted by the device. In some embodiments, the stored information may correspond to a different level of consent than the transmitted information, providing yet another level of granularity. Although the above example provides for three levels of consent, more or less than three levels of consent are contemplated within the scope and spirit of this disclosure. In this manner, management of patient/user consent may be provided in the context of the mDNA chromosomes.

Although the various different chromosomes are provided as a non-exhaustive example above, some embodiments provide that which of the chromosomes are collected, gathered, and/or detected may correspond to regulatory requirements. As such, different subsets of chromosomes may be received corresponding to different regulatory environments. Some embodiments provide that the device chromosomes may be used to provide device specific identifying information that may be associated with all information received, retrieved, gathered, detected and/or generated, among others. For example, device specific serial numbers, telephone numbers, and/or other addresses or identifiers may be associated with the other information gathered. In some embodiments, a mobile device screen size and/or resolution may be used to render a scale on all devices and/or types thereof to represent the exact and/or substantially the same physical size of the scale so that the scale may be interpreted consistently among the devices and/or types thereof regardless of screen size. In this manner, regulatory compliance corresponding to such functionality may be supported.

The chromosomes may be gathered via a communication resulting from receiving an initial contact via the mobile terminal. Once a message is received from the mobile terminal, initial details corresponding to the user and the device may be received and/or collected. Non-limiting examples of data collection, gathering and/or detection mechanisms may include browser user agent strings, browser user agent profile identifiers such as uniform resource identifier (URI) or uniform resource locator (URL), near field identification techniques, text messaging, multimedia messaging, and/or voice recognition (collecting user mDNA), among others. In some embodiments, third party applications may be called to gather some chromosomes while some embodiments provide that some chromosomes may be gathered using device-executable code and/or scripts on the mobile terminal.

A unique identifier is associated with the user and/or device and with the chromosomes (block 106). As described herein, the unique identifier may be referred to as a mobile DNA tag (mDNA tag). The collected chromosomes may be encrypted (block 108) and stored with the mDNA tag in an encrypted database (block 110). Some embodiments provide that the mDNA tag may be stored in a database, on the mobile terminal and/or in a peripheral device, such as may be part of a BAN. Additionally, multiple mDNA tags may be generated corresponding to devices and or users. For example, a user mDNA tag may be associated with chromosomes corresponding to the user such that the user may interface with the system via different mobile terminals. Similarly, a device mDNA tag may be specific to a device and may include profile information corresponding to a specific user in the context of that device.

Some embodiments provide that the use of the encryption and the mDNA tag provides a de-identification function for protecting the user's identity and privacy. In this manner, de-identification may provide that the user is uniquely identified without storing a user's electronic personal health identifier (ePHI), such as a phone number or email address, among others. Some embodiments provide that some of the user's electronic personal health identifier (ePHI), such as a phone number, email address, disease condition, disease treatments, date of birth, etc. and/or any combination thereof may be encrypted and then stored. In the context of the device mDNA tag, device details corresponding to the mobile terminal may be de-identified. Additionally, by encrypting the chromosomes and providing the unique identifier, the identity of the user may be securely maintained, while the data may be preserved for any later disease progression analysis and/or cross-clinical study data analysis in order to provide more personal care for the patient. Some embodiments provide that in addition to encrypting data, the data field identifiers may also be encrypted. In this manner, not only is the information difficult to resolve without decryption, but the nature and/or format of the data is also difficult to resolve.

The secure nature of the mDNA may be used to provide, supplement and/or enhance a variety of functions. For example fraud detection and/or prevention may be improved by ensuring that the proper mobile access is given to an electronic medical records (EMR) system and/or information therein. Additionally, location data used in conjunction with mDNA may provide an additional layer of confirmation and/or may generate an alert regarding access to an EMR system, electronic clinical data and/or other data that is to remain secure. Some embodiments provide that the mDNA may be used heuristically to determine habits and/or deviations therefrom to signal that a mobile device may have been stolen and/or misappropriated and thus may no longer be associated with the user. Additionally, mDNA metrics may be customized to provide alerts and/or thresholds for alerts regarding the security of the device and/or user. For example, drastic changes in contacts and/or social network activity may generate an alert. Further, since mDNA may include that corresponding to a physician or service provider, analysis of their mDNA may be used to determine that access to EMRs is authorized and/or compliant.

Further, some embodiments provide that an mDNA profile of a user may be used to provide personalized communications to that user. For example, patient announcements based on location, for example proximity to a particular pharmacy, may be sent. Additionally, announcements, such as, for example, Tweets, may be filtered by the mDNA profile to only receive relevant announcements, for example, those based on the patient's condition. Similarly, based on an mDNA profile, information corresponding to clinical studies and/or new treatments and/or drugs that may be available may be identified and sent to the user. Further, device chromosomes corresponding to the appearance and/or theme of the device may be used to present information in a format that is consistent therewith, even to the extent of the arrangement of icons or other types of user interface functional components.

Figure 2:
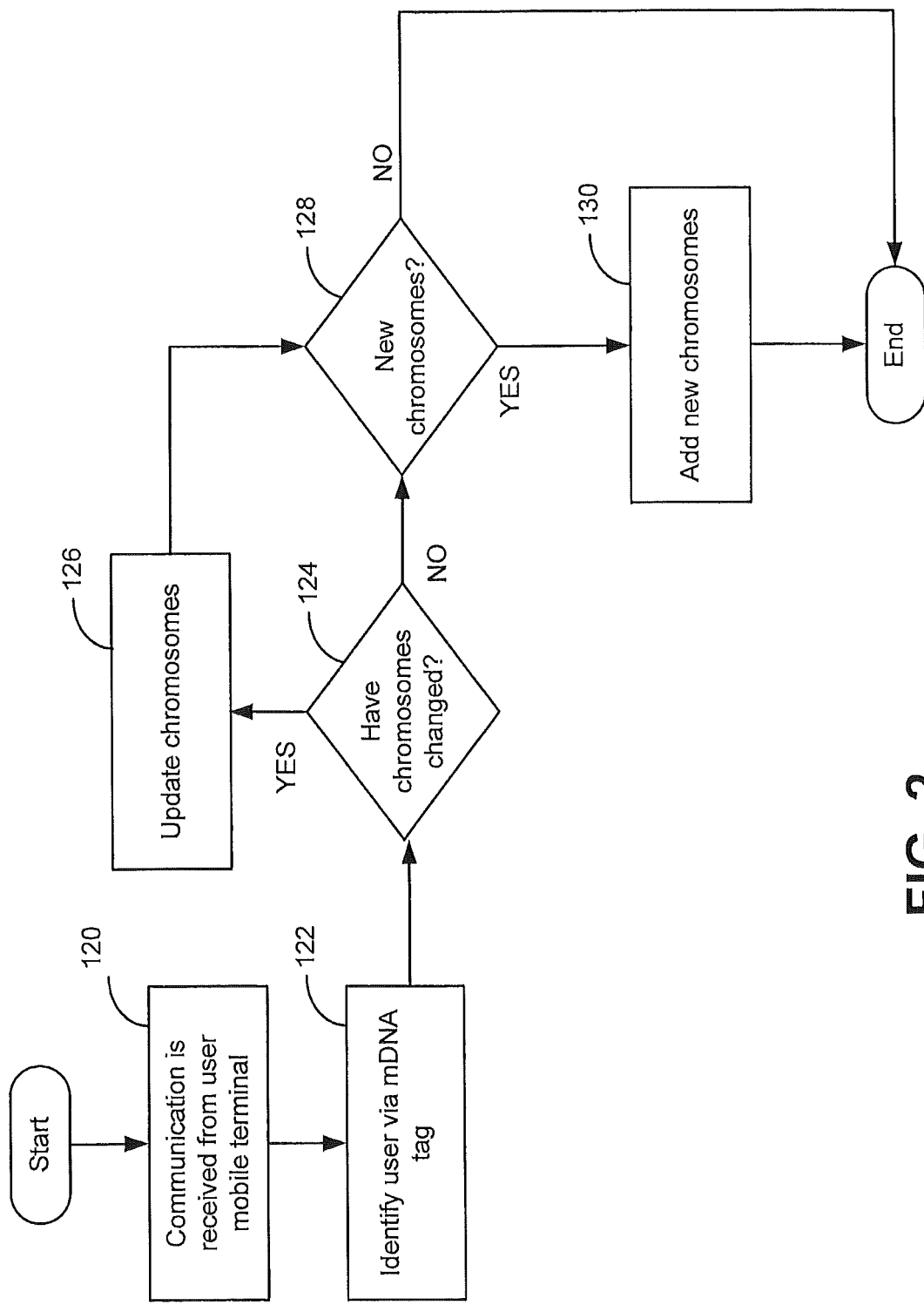
FIG. 2 is a block diagram illustrating updating chromosomes in accordance with some embodiments of the present invention.

Brief reference is now made to FIG. 2, which is a block diagram illustrating updating chromosomes in accordance with some embodiments of the present invention. Some embodiments provide that subsequent communications with the device may gather, associate and store more chromosomes and/or updated chromosome data. For example, a communication is received from the user mobile terminal. (block 120). The user may be identified using the unique mDNA tag (block 122) and a determination may be made as to whether any of the chromosomes have changed (block 124). If any of the chromosomes have changed, the changed chromosomes may be updated (block 126). If any of the chromosomes have been changed, a determination may be made as to whether any changes in service should be made responsive to the changed chromosome. Some embodiments provide that a determination may be made as to whether there are any new chromosomes (block 128). If there are new chromosomes, then the new chromosomes may be added (block 130). Although illustrated as operations that end, embodiments of the invention herein are not so limited. For example, the operations of FIG. 2 may be repeated at given time intervals during and/or between communications with a user and/or may be initiated responsive to communications with a user.

Some embodiments provide that updating mDNA may include setting a flag to update an mDNA record the next time the device is communicatively coupled to the solution provider and/or to set time intervals for checking for updated mDNA data of the device. In this manner, new chromosomes may be updated while the general profile may remain the same. In some embodiments, some device chromosomes may be determined as backwardly compatible while others may not. As such, an upgrade of firmware to one version may be determined as being backwardly compatible and thus no action may be warranted. In contrast, an upgrade to another version of firmware than is not backwardly compatible may result in a recommendation to provide the user with a new device.

Further, a user chromosome may be updated to reflect that the user is illiterate, based on, for example, a response to a text code. In this example, further communication to the user may be provided using a voice based service that may dial the user and provide oral as opposed to written instructions on how to remain compliant. For example, reminders and/or instructions to take medication or attend appointments may be provided. Additionally, the oral communications may include a component of a larger disease education process, among others. Some embodiments provide that the illiterate chromosome may also be updated later in the event that the user learns to read, for example.

As disclosed above regarding FIG. 1, the collected chromosomes the mDNA tag may be stored in a database, which may be referred to herein as an mDNA database. Additionally, some embodiments provide that a separate database may be provided that may include selected information corresponding to a user mDNA profile that may be utilized in conjunction with medical expertise to provide medical solutions to users. In this regard, a therapy database may be provided. Examples of a therapy based approach may include indicating which form of communication is more suitable for patients who have been diagnosed with Alzheimer's disease. For example, some circumstance indicate that care givers be given access to patient data. In the case where a patient is visually impaired, communication may be provided via voice and/or audible forms. Additionally, some cases dictate that accessibility options on the mobile device should be checked before each communication with the user.

A user and/or device mDNA profile may be used to compile data and text usage per user and/or per device mDNA tag to detect and/or identify trends and/or metrics. Some embodiments provide that device mDNA metrics may be used to assist in the identification of new strategies for developing and/or providing content, solutions and/or applications. For example, some embodiments provide that device and/or user mDNA metrics may provide forward looking information regarding trends, such as, for example, medical trends. Additionally, in some embodiments, the health and/or functionality of a device may be detected using metrics from device mDNA that may be used to trigger an alert regarding decreased device performance and/or the security thereof. Examples of how such metrics may be used include simple fixed and/or variable threshold, a statistical model, and/or a computationally intelligent tool such as neural networks, among others.

Yet further, mDNA may customize the experience based on the user and/or device mDNA to improve patient compliance with study and/or treatment regimens. For example, medication compliance may be improved using mDNA on a device by providing an application that can capture a still image of a barcode on packaging that defines a dosing regimen. Additionally, study related materials may include barcodes that provide sample tracking.

Some embodiments provide that the mDNA data may prove and/or authenticate that content, applications and/or solutions are validated for each device. For example if mDNA is part of a labeling claims for a licensed drug, then specific provisions may be made for dosing control and/or other regimen controlling functions and the use of any telephony support may interact with mDNA to determine appropriate content, applications, and/or solutions.

In some embodiments, mDNA may enable more secure presentation of data by detecting and/or identifying weaknesses in protocols and security. For example, some embodiments provide that mDNA may provide a physician with the option of using her own device on a ward to securely interface with patient records. Some embodiments provide a hierarchy of security levels in which a physician may have superior rights to access data once the patient has opted in to sharing that data. In some embodiments, a physician may be notified of security gaps and/or risks of regulatory non-compliance and may be provided with recommendations for corrective actions responsive thereto.

Some embodiments may identify a video format that is supported on the handset to facilitate physician communication. For example, a physician may send a video message to a patient device that includes medical and/or healthcare instructions. In some embodiments, the video may further include a viewing confirmation sequence such as "text the code 15442" in the last several frames of the video. In this manner, the physician may confirm that the patient has viewed the video message.

In some embodiments, the device chromosomes corresponding to signal strength and network capabilities may be used to determine a dependability hierarchy of different operations and/or technologies for sending and/or receiving data to/from the device. For example, if a GPRS data connection is weak and deemed unreliable for transmitting data, then the data may be transmitted via a text message and/or via a WiFi transmission.

Some embodiments provide that mDNA tags of multiple users may be linked to form a community and/or team. For example, a team may include a patient, a caregiver, a physician and/or an insurance provider and may each be provided the correct level of access to shared data between mobile devices.

In some embodiments, if a user is determined to be outside an identified service area, a caregiver may be contacted to and provided location data so the user and/or patient requires assistance. For example, this application may be particularly useful in the case of patients suffering from dementia or other cognitive impairments.

Figure 3:
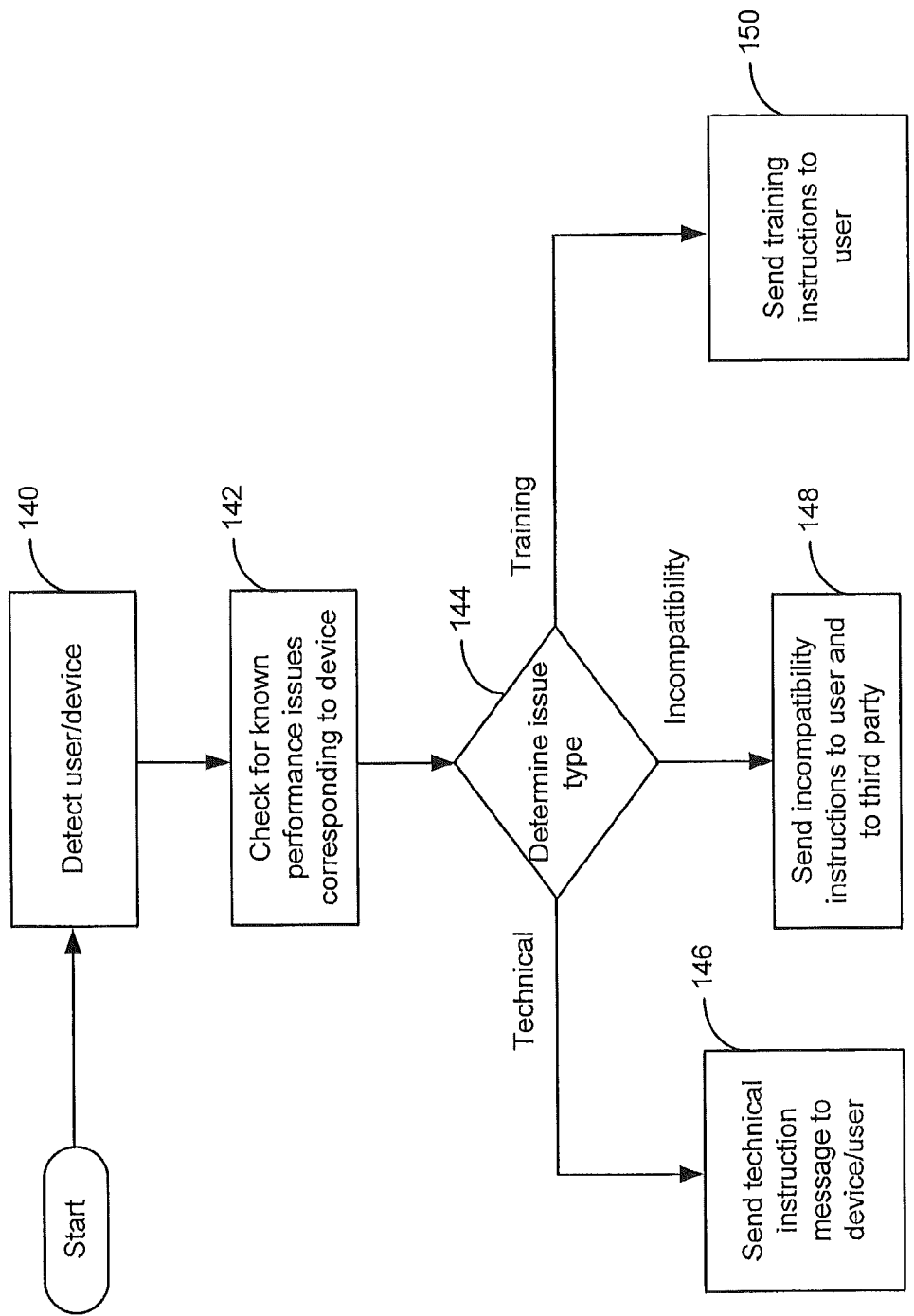
FIG. 3 is a block diagram of operations corresponding to using mDNA to determine and/or identify technical issues corresponding to a user's mobile terminal according to some embodiments of the present invention.

Reference is now made to FIG. 3, which is a block diagram of operations corresponding to using mDNA to determine and/or identify technical issues corresponding to a user's mobile terminal according to some embodiments of the present invention. In some embodiments, operations may include detecting a user and/or a user device (block 140). The user device may include a mobile and/or fixed terminal that includes and/or is communicatively coupled to at least one processor. In some embodiments, a device may include a subject device corresponding to a subject participating in a clinical study. Some embodiments provide that a mobile terminal may include a personal digital assistant (PDA), cell phone, pager and/or a machine that does not include a direct human communication interface in order to service a remote area and/or one in which a user may not have a persistent or reliable data connection, The mobile terminal may provide that mDNA data may be stored in a fixed memory location in the mobile terminal and/or may be stored in a removable media. Additionally, some embodiments provide that removable storage media may be used to transmit data to the mobile terminal using a physical delivery system.

A check for known performance issues corresponding to the device may be performed (block 142). In some embodiments, a database that includes known and/or previously determined and/or identified issues corresponding attributes corresponding to specific device manufacturers, models, operating systems, interfaces, applications, versions, may be generated, updated and/or accessed to document, record, and/or identify performance issues. For example, as mDNA is gathered and used, a particular device attribute may be determined as causing one or more performance issues. As such, a database may be populated with such attributes and the identified performance issues. Further, some embodiments provide that the database may include one or more solutions for overcoming and/or resolving the performance issues.

Responsive to identifying any known performance issues with the device, the issue type may be determined (block 144). If the issue type is identified as a technical issue, then a message including a technical instruction and/or data file may be sent to the user (block 146). For example, a message such as "Please install this patch to correct the security issue on your device" may be sent along with a file that resolves the identified performance issue. If the issue type is incompatibility (e.g., it is determined from mDNA that an application may not execute properly on the user device), a message including incompatibility instructions may be sent to the user and/or to a third party (block 148). For example, in the context of a healthcare related application such as a pharmaceutical trial, campaign or study, a third party may include a healthcare industry professional and/or representative or agent thereof. An example of such a message may include "Please provide the subject with one of the study handsets and update the contact information for the study subject to include the new handset number." Additionally and/or alternatively the user may be sent a message such as "Please show the following message to your health care provider <title> <first name> <last name> Please provide the patient with one of the study handsets and update the contact information for the study subject to include the new handset number." In this manner, a user may be provided a device that has been procured as a back-up for incompatible user devices and that is compatible with the applications and/or solutions to be provided. If the issue type is a training issue, the user may be sent a message that includes training instructions (block 150). For example, a training instruction may state "The cellular signal on your phone is low, please go to a window or outside to get a better signal or connect to WiFi." In some embodiments, a third party may be sent instructions to provide additional training to the user.

Although specific examples of messages are provided above, such examples are non-limiting in that a message may include one or more of a text message, an email message, a multimedia message, an application notification that is generated from one or more applications, a mobile terminal specific notification, an audible notification, a visually perceptible and/or a vibratory notification, among others.

Figure 4:
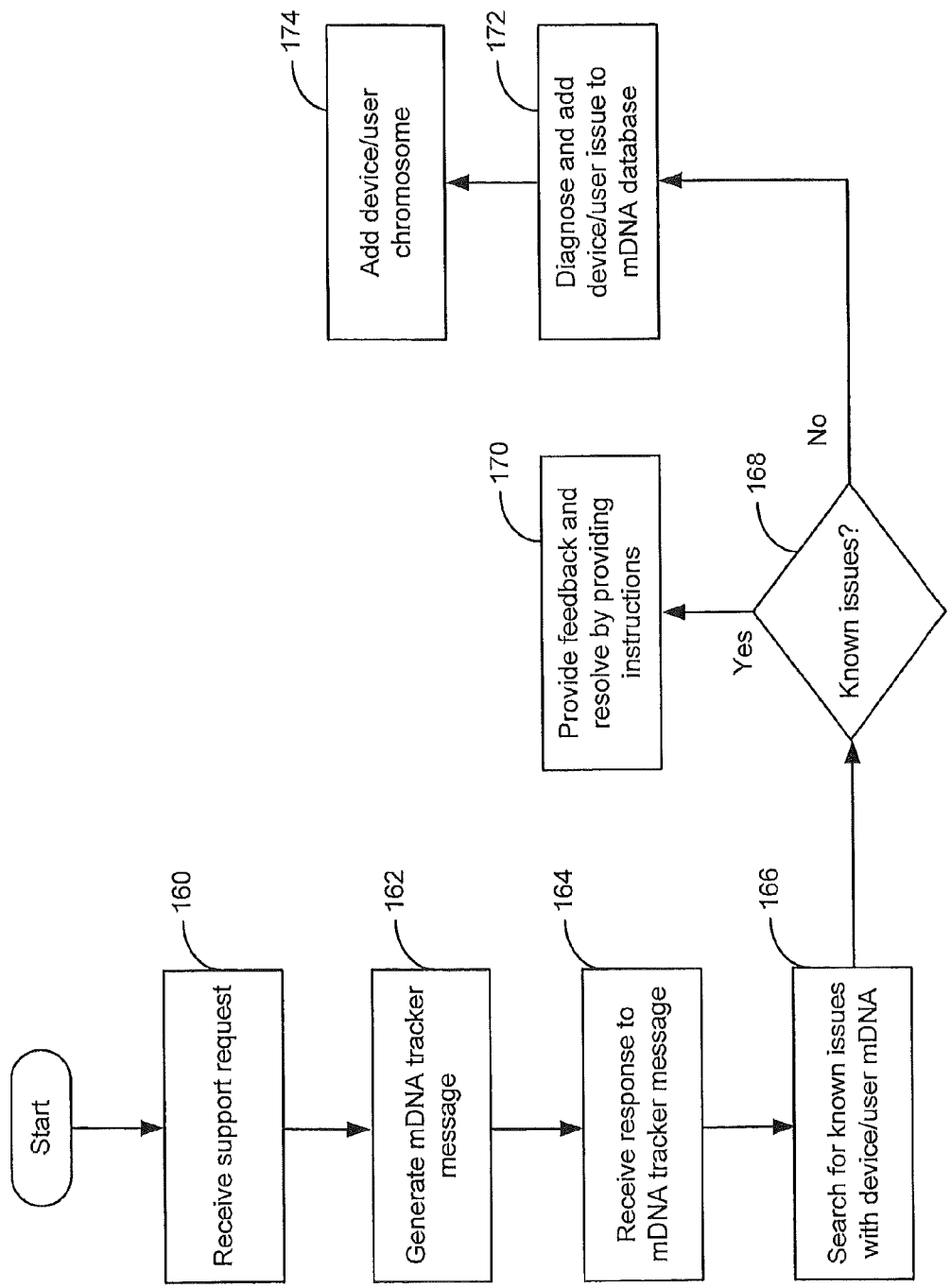
FIG. 4 is a block diagram illustrating operations for providing device support using mDNA according to some embodiments of the present invention.

In addition to identifying device performance issues, mDNA systems methods and computer program products may also be used to provide device support. For example, reference is now made to FIG. 4, which is a block diagram illustrating operations for providing device support using mDNA according to some embodiments of the present invention. A support request corresponding to a device such as a mobile terminal may be received (block 160). In this context, the device/user may have already been enrolled and at least an initial determination of the specific mDNA is already detected and/or stored. The support request may be initiated by a user, subject, and/or third party and/or sponsor of a campaign or study in which the user is enrolled. An mDNA tracker message may be generated responsive to receiving the support request (block 162). A response to the mDNA tracker message may be received (block 164). In some embodiments, the response may be received as a result of the user clicking or executing an active link, opening an application and/or responding to and/or via a text message.

A search for known issues with the device and/or user mDNA may be performed (block 166) and a determination regarding known issues is made (block 168). If there are known issues associated with the device and/or user mDNA, then feedback may be provided and the issue may be resolved by providing instructions (block 170). If there are no known issues, then diagnosis is performed and the device/user issue is added to the mDNA database (block 172). In some embodiments, operations for providing device support may be performed automatically using a computational intelligent agent. Some embodiments provide that operations for providing device support may be performed using a processor that executes a program corresponding to a decision tree type of problem identification and resolution. In order to determine a solution for an unknown issue quickly, the user manual for the mobile device is automatically located and/or stored as part of the mDNA.

Figure 5:
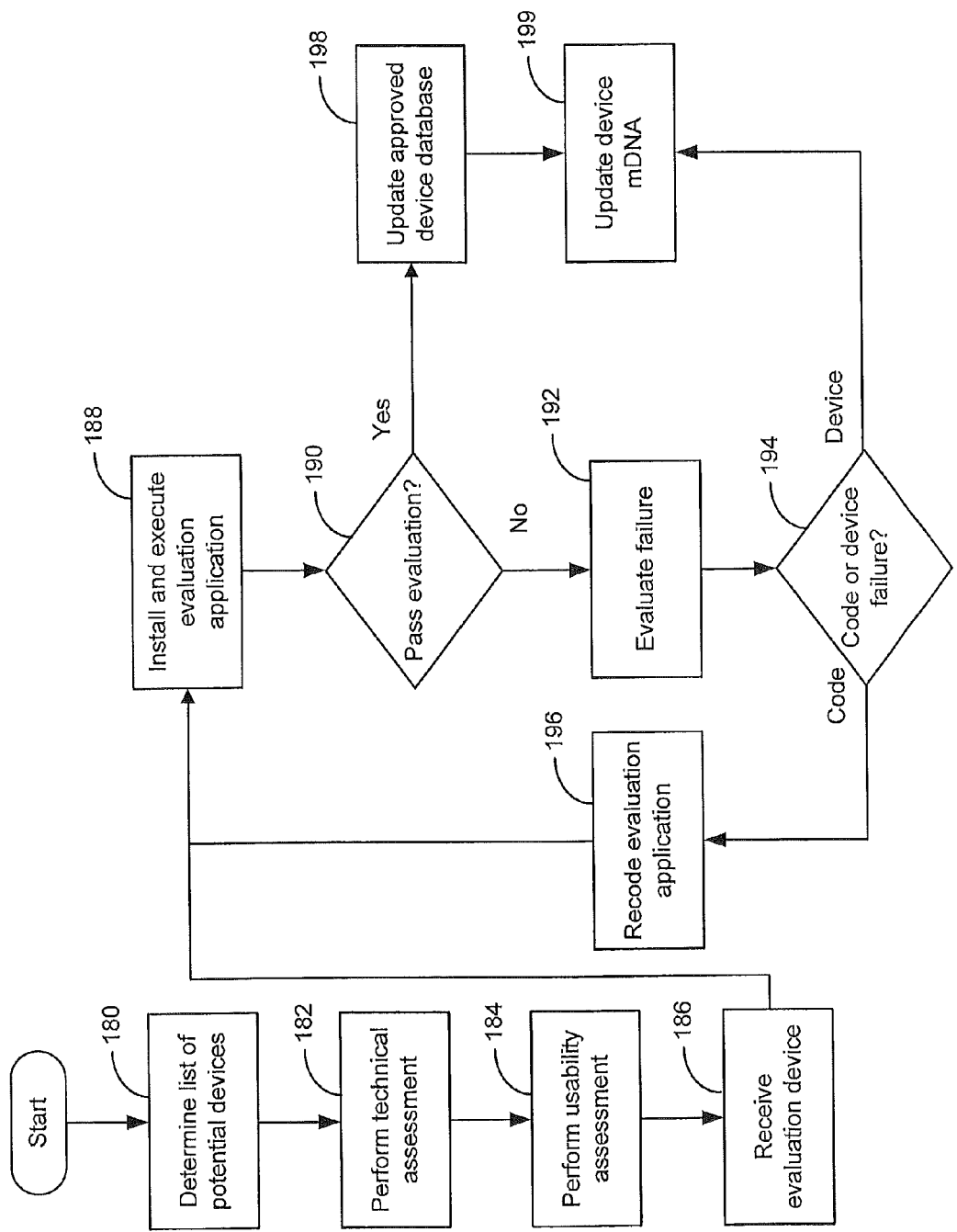
FIG. 5 is a block diagram illustrating operations that may be performed to evaluate a device such as a mobile terminal, for delivering an application and/or solution.

As part of a continual evaluation of devices that can be used for campaigns such as clinical trials, issues that are identified during evaluation may be associated with the device and/or a device attribute and logged. For example, reference is now made to FIG. 5, which is a block diagram illustrating operations that may be performed to evaluate a device such as a mobile terminal, for delivering an application and/or solution. A list of potential devices may be determined (block 180). In some embodiments, determining the list may include preliminary operations including submitting a definition of minimum requirements to a potential supplier and receiving a list of potential devices to consider. Based on the list of potential devices, a technical assessment of at least one device may be determined (block 182). Additionally, a usability assessment of the at least one device may be determined (block 184). An evaluation device may be received (block 186) and at least one evaluation application may be loaded and executed thereon (block 188). A determination is made as to whether the device passes the evaluation (block 190). If the device passes the evaluation, then an approved device database is updated (block 198) and the device mDNA is updated (block 199).

If the device does not pass the evaluation, then the source and/or type of failure is evaluated (block 192). A determination is made as to whether the code was the source of failure or the device was the source of failure (block 194). If the code was the source of failure, then the evaluation application may be recoded (block 196) and evaluation may be repeated according to the operations described above regarding blocks 188, 190, 192, etc. If the device is the source of failure then the device mDNA is updated (block 199).

Once the mDNA is acquired, some embodiments include providing device specific content, applications and/or solutions. Some embodiments provide that when a device is connected to a solution provider system, the device is identified and the mDNA chromosomes may be looked using the identity. In some embodiments, mDNA includes a modular construction such that applications that are internal and/or external to mDNA and/or the solution provider may access the mDNA service. Some embodiments provide that mDNA may be used to look-up chromosomes directly from the database and/or may be used to determine chromosomes dynamically by an application at the time that the application connects to, is installed on and/or otherwise communicates with the mobile device. Once the device's chromosomes are available, the solution provider may use the chromosome data to provide, improve and/or correct content, applications and/or solutions to be provided to the device. By way of example, a screen size chromosome may provide information sufficient to optimize the display functionality corresponding to the content, application and/or solution. Similarly, a different content type may be provided responsive to determining a content support chromosome. For example, the device may be capable of supporting a particular video format and/or may or may not be capable of processing streaming video. In some embodiments, a calendar type may be detected so that appointments and/or reminders may be sent and/or stored in a format that is consistent with that calendar type. Additionally, a user and/or device mDNA profile may be used to determine if the user has unlimited or prepaid text messaging and/or data services. In this regard, a determination may be made as to whether a free or sender paid text and/or data service may be applied. Some embodiments provide that mDNA data and/or an application accessed thereby may be used to track how much data and/or how many messages are received/sent corresponding to one or more specific studies and/or campaigns.

Some embodiments provide that an application may be selected based on one or more chromosomes. For example, an application version may be selected from an application database and/or an application may be compiled to corresponding to an application framework that is compatible with any user-specific chromosomes. In some embodiments, user and/or device mDNA may be used to determine if any device functions should be disabled and/or enabled to provision compliant receipt of content, solutions and/or applications.

Figure 6:
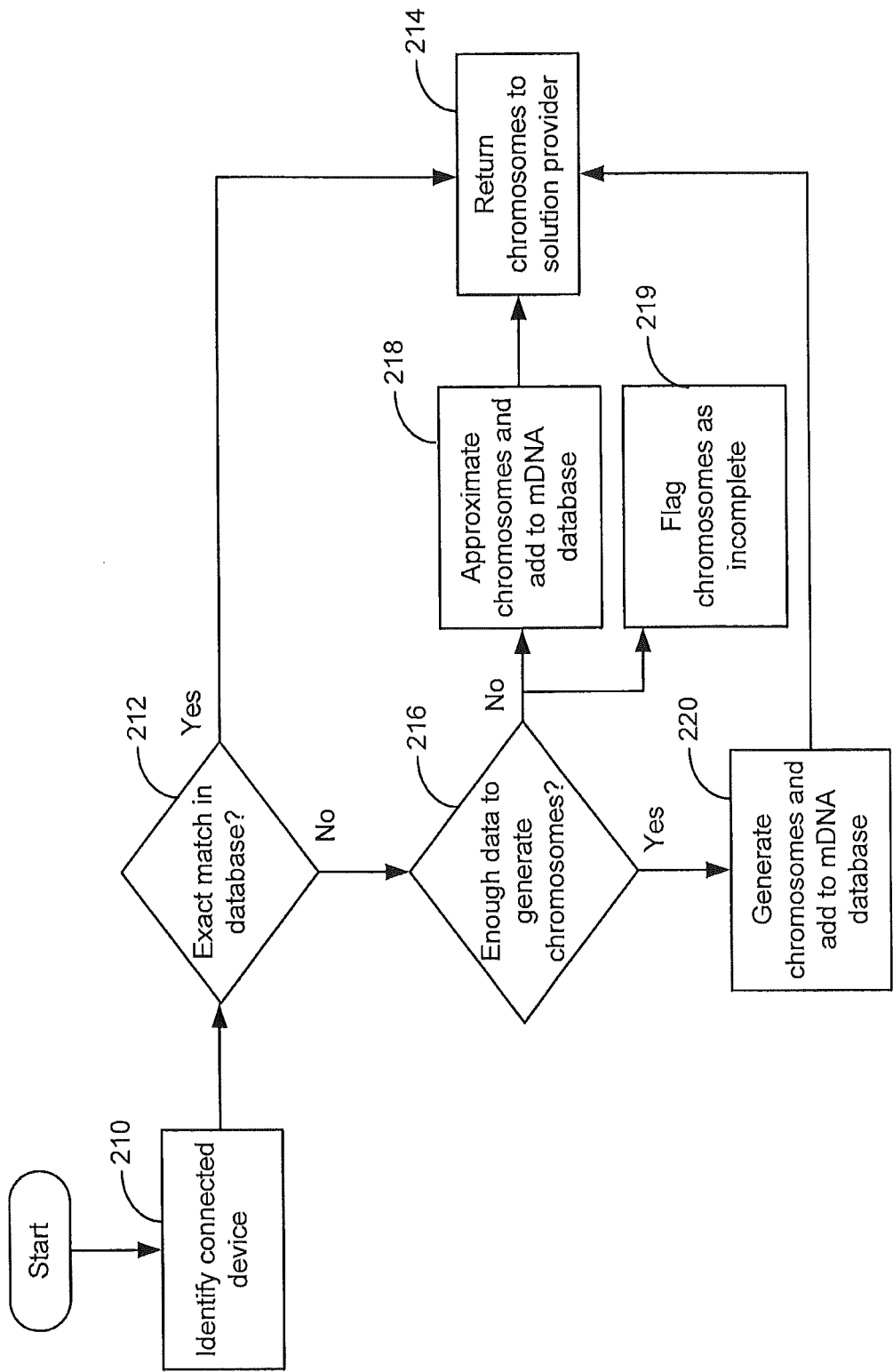
FIG. 6 is a block diagram illustrating operations for adding new devices to an mDNA database according to some embodiments of the present invention.

Some embodiments provide that new devices may be automatically added to an mDNA database. For example, reference is now made to FIG. 6, which is a block diagram illustrating operations for adding new devices to an mDNA database according to some embodiments of the present invention. When a device is connected to a solution provider, the solution provider may identify the connected device (block 210). For example, the device may be identified by manufacturer, model identifier, communication and/or data network service provider and/or operating system, among others. A determination is made as to whether a database that includes device information and/or chromosomes includes an exact match to the connected device (block 212). If the database includes an exact match to the connected device, then other chromosomes corresponding to the connected device are returned to the solution provider (block 214). If there is no exact match to the connected device, then a determination may be made as to whether there is enough data to generate chromosomes corresponding to the connected device (block 216). If there is sufficient data, the chromosomes corresponding to the connected device are generated and added to the mDNA database (block 220). The generated chromosome may returned to the solution provider for use in providing the content, solutions and/or applications (block 214). If there is not enough data to generate chromosomes, the chromosomes may be approximated and the approximated chromosomes may be added to the mDNA database (block 218). Some embodiments provide that if there is not enough data to generate chromosomes, missing chromosomes may be flagged as incomplete (block 219). The approximated chromosomes may then be returned to the solution provider for use in providing content, solutions and/or applications.

In use and operation, the systems, methods and computer program products corresponding to mDNA, may be accessible to customers such as campaign and/or study sponsors, healthcare professionals, etc. In this regard, secure access may be provided to such customers to supplement and/or increase the value of their existing systems. For example, an Electronic Medical Records system used by a customer may integrate with mDNA to determine a best mobile solution to help a patient with diabetes who may use one or more peripheral devices for blood monitoring, depending on the type and/or configuration of the device that the patient uses. For example, a solution for a patient with a Nokia mobile terminal may be distinct from a solution for a patient with a Motorola mobile terminal.

Figure 7:
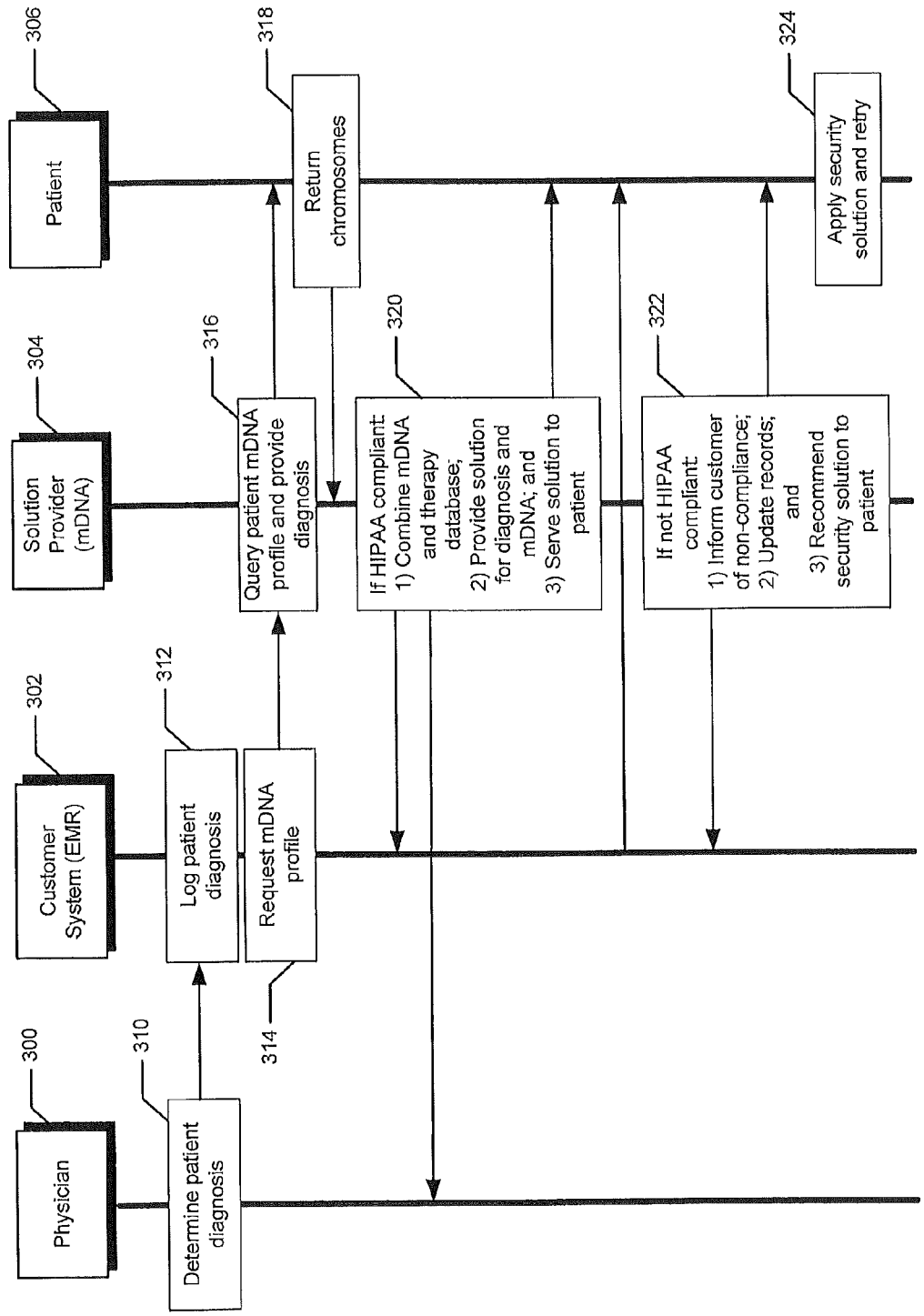
FIG. 7 is a block diagram illustrating data flows for an example of customer integration with an mDNA system according to some embodiments of the present invention.

Reference is now made to FIG. 7, which is a block diagram illustrating data flows for an example of customer integration with an mDNA system according to some embodiments of the present invention. A physician 300 may determine a patient diagnosis (block 310), which may be provided to a customer system 302, such as an electronic medical records (EMR) system, among others. The patient diagnosis is logged by the customer system 302 (block 312). The customer system 302 requests an mDNA profile of the patient 300 from a solution provider (e.g., mDNA) 304 in order to provide access to the patient's data via the patient's mobile device (block 314). The solution provider 304 queries the patient (e.g., the patient's device(s)) for the mDNA profile and provides the diagnosis to the patient 306 (block 316). Chromosomes are returned to the solution provider 304 (block 318).

The solution provider 304 then determines if the patient device is capable of compliant delivery of the solution. For example, some embodiments provide that compliance with HIPAA regulations may be determined. If the device is compliant, then the mDNA and therapy database information may be combined, the solution for diagnosis and mDNA may be provided and the solution may be served to the patient (block 320). If the device is not capable and/or configured to provide a compliant solution, then the customer system 302 may be informed, the records may be updated to document the non-compliance and/or the source thereof, and a recommended security solution may be sent to the patient 306 (block 322). Although illustrated as being provided by the solution provider 304, some embodiments provide that selective operations corresponding to blocks 320 and/or 322 and/or portions thereof may be provided via the customer system 302. For example, in some embodiments, a customer system 302 may be integrated to perform some of the disclosed operations that may be supported by data, services, and/or oversight of the solution provider 304. The patient 306 may apply the security solution and the evaluation and solution process may be repeated (block 324). For example, operations may repeat starting with requesting the mDNA profile as discussed above regarding block 314.

The foregoing is illustrative of the present invention and is not to be construed as limiting thereof. Although a few embodiments of the present invention have been described, those skilled in the art will readily appreciate that many modifications are possible in the embodiments without materially departing from the novel teachings and advantages of the present invention. Accordingly, all such modifications are intended to be included within the scope of the present invention as defined in the claims. Therefore, it is to be understood that the foregoing is illustrative of the present invention and is not to be construed as limited to the embodiments disclosed herein, and that modifications to the disclosed embodiments, as well as other embodiments, are intended to be included within the scope of the appended claims. The present invention is defined by the following claims.

That which is claimed is:

1. A method of providing device independent compliant applications, the method comprising:

receiving device data corresponding to a mobile device that is operable to be connected to a solution provider, wherein the mobile device is at least one of a cell phone or a personal digital assistant (PDA);

receiving user data corresponding to the user of the mobile device, wherein user data includes communication related data and personal identification data corresponding to the user, wherein the communication related data includes mobile device identification data corresponding to the mobile device;

receiving peripheral interface data that corresponds to peripheral devices that may interface with the mobile device corresponding to a user function, wherein peripheral interface data includes peripheral interface identification information;

associating the device data, the user data and the peripheral interface data with a unique identifier;

encrypting at least a portion of the device data, the user data, and/or the peripheral interface data;

storing the unique identifier and at least a portion of the device data, the user data and/or the peripheral data;

de-identifying the user by storing the unique identifier separate from the device data, the user data and/or the peripheral data; and updating the device data, the user data and/or the peripheral interface data by setting a flag to update the device data, the user data and/or the peripheral interface data the next time the device is communicatively coupled to a solution provider, wherein the user is de-identified relative to the device data, the user data, and the peripheral data and the device data, the user data and the peripheral data are available for use in subsequent analyses, wherein at least one of receiving device data, receiving user data, receiving peripheral interface data, associating the device data, the user data and the peripheral interface data, the encrypting and the storing is performed using at least one processor.

2. The method according to claim 1, wherein receiving the device data comprises receiving device manufacturer identification data, a device model number, a device version identifier, and/or at least one display capability.

3. The method according to claim 1, wherein receiving the device data comprises receiving types and/or formats of supported media, at least one media streaming capability, image capturing functionality, a multimedia messaging service (MMS) capability and/or a digital rights management capability.

4. The method according to claim 1, wherein receiving the device data comprises receiving data corresponding to installed and/or supported applications and/or browser related data including user agent and user agent profile.

5. The method according to claim 1, wherein receiving the device data comprises receiving a communication capability including at least one of a near field communication (NFC) capability, a wireless and/or wired network communication capability, and a communication network capability.

6. The method according to claim 1, wherein receiving the device data comprises receiving at least one of data corresponding to markup languages, location awareness capability, encryption functionality, and security features.

7. The method according to claim 1, wherein receiving the user data corresponding to the user of the mobile device comprises receiving personal identification data including name, gender, ethnicity, date of birth, place of birth, citizenship, subscriber identity module (SIM) card identifier, residence information, mobile terminal numerical identifier, a country or region, and/or a language preference.

8. The method according to claim 1, wherein receiving the user data corresponding to the user of the mobile device comprises receiving a list of installed and/or accessed applications, an identifier corresponding to a third party application, and/or communication service terms.

9. The method according to claim 1, wherein receiving the peripheral interface data comprises receiving parental interface identifiers, device sensor interfaces, and/or device alerts.

10. The method according to claim 1, wherein receiving the peripheral interface data comprises receiving data corresponding to medical diagnostic devices.

11. The method according to claim 1, wherein receiving the peripheral interface data comprises receiving a batch of peripheral interface data that is logged and stored by at least one of the peripheral devices.

12. The method according to claim 1, wherein receiving the peripheral device data comprises receiving a first subset of the peripheral interface data that is compliant in a first regulatory environment, wherein a second subset of the peripheral interface data that is different from the first subset of peripheral interface data is excluded.

13. The method according to claim 1, further comprising receiving updated device data, updated user data and/or updated peripheral interface data and storing the unique identifier and at least a portion of the updated device data, the updated user data and/or the updated peripheral interface data.

14. The method according to claim 1, further comprising generating an audit trail that is associated with operations corresponding to device data, user data, peripheral interface data, and/or the unique identifier.

15. The method according to claim 1, before receiving device data, receiving user data, or receiving peripheral interface data, further comprising receiving consent data that corresponds to at least a portion of the device data, the user data and/or the peripheral interface data.

16. The method according to claim 15, wherein the consent data includes a plurality of consent levels that respectively correspond to a plurality of different data types.

17. The method according to claim 16,
wherein a first consent level of the plurality of consent levels corresponds to device specific information regarding a specific device and/or type, and
wherein a second consent level of the plurality of consent levels corresponds to device personalization information.

18. A computer program product for providing device independent compliant applications, the computer program product comprising a non-transitory computer-readable medium having executable computer-readable program code therein, the computer-readable program code being configured to implement the method of claim 1.

19. A method of providing device independent compliant applications, the method comprising:
accumulating device, user and peripheral interface data corresponding to a mobile terminal of a user, wherein the mobile terminal is at least one of a cell phone or a personal digital assistant (PDA);
associating the device, user and peripheral interface data with a unique identifier and storing the device, user and peripheral interface data and the unique identifier in a database;
before storing the device, user and peripheral interface data, de-identifying the device, user and peripheral interface data based on the association with the unique identifier by storing the unique identifier separate from the device data, the user data and/or the peripheral data; and
updating the device data, the user data and/or the peripheral interface data by setting a flag to update the device data, the user data and/or the peripheral interface data the next time the device is communicatively coupled to a solution provider,
wherein the user is de-identified relative to the device data, the user data, and the peripheral data and the device data, the user data and the peripheral data are available for use in subsequent analyses, and
wherein at least one of accumulating the device, user and peripheral interface data, associating the device, user and peripheral interface data with the unique identifier, and before storing the device, user and peripheral interface data, de-identifying the device, user and peripheral interface data is performed using at least one processor.

20. The method according to claim 19, wherein accumulating device, user and peripheral interface data comprises receiving device manufacturer identification data, a device model number, a device version identifier, and/or at least one display capability.

21. The method according to claim 19, wherein accumulating device, user and peripheral interface data comprises receiving types and/or formats of supported media, at least one media streaming capability, image capturing functionality, a multimedia messaging service (MMS) capability, data corresponding to installed and/or supported applications and/or browser related data including user agent and user agent profile, a communication capability including at least one of a near field communication (NFC) capability, a wireless and/or wired network communication capability, and a communication network capability.

22. The method according to claim 19, wherein accumulating device, user and peripheral interface data comprises receiving personal identification data, a list of installed and/or accessed applications, an identifier corresponding to a third party application, and/or communication service terms.

23. The method according to claim 19, wherein accumulating device, user and peripheral interface data comprises receiving parental interface identifiers, device sensor interfaces, device alerts, data corresponding medical diagnostic devices and/or a batch of peripheral interface data that is logged and stored by at least one of the peripheral devices.

24. The method according to claim 19, further comprising generating an audit trail that is associated with operations corresponding to device data, user data, peripheral interface data, and/or the unique identifier.

25. The method according to claim 19, wherein de-identifying the device, user and peripheral interface data comprises encrypting at least a portion of the device, user and/or peripheral interface data and storing the encrypted data in association with the unique identifier.

26. The method according to claim 25, wherein de-identifying the device, user and peripheral interface data comprises encrypting at least one of a plurality of data field identifiers under which the encrypted data is stored.

27. The method according to claim 19, further comprising determining a type and/or format responsive to the device, user and/or peripheral interface data.

28. A computer program product for providing device independent compliant applications, the computer program product comprising a non-transitory computer-readable medium having executable computer-readable program code therein, the computer-readable program code being configured to implement the method of claim 19.

29. The method according to claim 1, wherein the unique identifier is associated with a specific mobile terminal and includes information corresponding to the user in the context of the specific mobile terminal.

* * * * *